United States Patent
Liu et al.

(10) Patent No.: US 8,716,268 B2
(45) Date of Patent: May 6, 2014

(54) NITRATE ESTERS OF CORTICOID COMPOUNDS USEFUL AS DIURETICS

(76) Inventors: Chao Liu, Shijiazhuang (CN); Kunshen Liu, Shijiazhunag (CN)

( * ) Notice: Subject to any disclaimer, the term of this patent is extended or adjusted under 35 U.S.C. 154(b) by 243 days.

(21) Appl. No.: 13/151,628

(22) Filed: Jun. 2, 2011

(65) Prior Publication Data

US 2011/0301136 A1    Dec. 8, 2011

Related U.S. Application Data

(60) Provisional application No. 61/352,254, filed on Jun. 7, 2010.

(51) Int. Cl.
| | | |
|---|---|---|
| *A61K 31/56* | (2006.01) | |
| *A61K 31/567* | (2006.01) | |
| *A61K 31/573* | (2006.01) | |
| *A61K 31/575* | (2006.01) | |

(52) U.S. Cl.
CPC ............. *A61K 31/567* (2013.01); *A61K 31/573* (2013.01); *A61K 31/575* (2013.01)
USPC ............................ 514/170; 514/180; 514/182

(58) Field of Classification Search
CPC .. A61K 31/567; A61K 31/573; A61K 31/575
USPC .......................................... 514/170, 180, 182
See application file for complete search history.

(56) References Cited

U.S. PATENT DOCUMENTS

| | | |
|---|---|---|
| 3,494,941 A | 2/1970 | Ledig et al. |
| 5,824,669 A | 10/1998 | Garvey et al. |
| 5,837,698 A | 11/1998 | Tjoeng et al. |
| 6,197,762 B1 | 3/2001 | Garvey et al. |
| 6,579,863 B1 | 6/2003 | Garvey et al. |
| 6,610,676 B1 | 8/2003 | Del Soldato |
| 7,056,905 B2 | 6/2006 | Del Soldato |
| 7,157,450 B2 | 1/2007 | Del Soldato |
| 7,160,871 B2 | 1/2007 | Del Soldato |
| 7,196,075 B2 | 3/2007 | Del Soldato |
| 7,205,288 B2 | 4/2007 | Del Soldato |
| 7,368,442 B2 | 5/2008 | Del Soldato |
| 7,605,151 B2 | 10/2009 | Del Soldato |
| 2005/0004089 A1 | 1/2005 | Soldato |

FOREIGN PATENT DOCUMENTS

| | | |
|---|---|---|
| EP | 0929565 | 7/1999 |
| FR | 2143664 A1 | 2/1973 |
| WO | 9815568 A2 | 4/1998 |
| WO | 0049993 A2 | 8/2000 |
| WO | WO0049993 | 8/2000 |
| WO | 03064443 A2 | 8/2003 |
| WO | 2010015529 A1 | 2/2010 |

OTHER PUBLICATIONS

Paul-Clark et al. 21-NO-prednisolone is a novel nitric oxide-releasing derivative of prednisolone with enhanced anti-inflammatory properties; British Journal of Pharmacology (2000) vol. 131, 1345-1354.
Paul-Clark et al. Glucocorticoid Receptor Nitration Leads to Enhanced Anti-Inflammatory Effects of Novel Steroid Ligands; The Journal of Immunology (2003) p. 3245-3252.
Paul-Clark et al. Potent antiarthritic properties of a glucocorticoid derivative, NCX-1015, in an experimental model of arthritis; PNAS Feb. 5, 2002 vol. 99 No. 3 1677-1682.
Liu et al. Potent Potentiating Diuretic Effects of Prednisone in Congestive Heart Failure; J Cardiovasc Pharmacol vol. 48, No. 4, Oct. 2006.
Di Fillipo et al. The Distinct Alterations Produced in Cardiovascular Functions by Prednisolone and Nitro-prednisolone (NCX-1015) in the Rat Highlight a Causal Role for Endothelin-1; The Journal of Pharmacology and Experimental Therapeutics vol. 310, No. 3 2004.
Liu et al. Potent Diuretic Effects of Prednisone in Heart Failure Patients with Refractory Diuretic Resistance; Can J Cardiol vol. 23 2007.
Sica et al. Diuretic Resistance and Strategies toOvercome Resistance in Patients With Congestive Heart Failure; Pharmacotherapy in CHF Mar./Apr. 2002.
Potter et al. Natriuretic Peptides, Their Receptors, and Cyclic Guanosine Monophosphate-Dependent Signaling Functions; Endocrine Reviews 27(1):47-72 2006.
A.J. De Bold et al. A Rapid and Potent Natriuretic Response to Intravenous Injection of Atrial Myocardial Extract in Rats; Life Sciences, vol. 28, pp. 89-94 Oct. 21, 1980.
Qiong Ye, Endothelin Inhibits NPR-A and Stimulates eNOS Gene Expression in Rat IMCD Cells; Journal of the American Hear Association Mar. 2003.
Robert W. Schrier et al. Hormones and Hemodynamics in Heart Failure; Mechanisms of Disease Aug. 19, 1999.
Haya Yechieli et al. Regulation of renal glomerular and papillary ANP receptors in rats with experimental heart failure; American Physiological Society 1993.
Paula M. Bryan et al. Renal hyporesponsiveness to atrial natriuretic peptide in congestive heart failure results from reduced atrial natriuretic peptide receptor concentrations; Am J Physiol Renal Physiol 292: F1636-F1644, 2007.
Jean-Baptiste Michel et al. Urinary cyclic guanosine monophosphate as an indicator of experimental congestive heart failure in rats; Cardiovascular Research, 1990, 24, 946952.
Liu Chao et al, "Potent Potentiating Diuretic Effects of Prednisone in Congestive Heart Failure", Journal of Cardiovascular Pharmacology, Oct. 1, 2006, 173-176, vol. 48 No. 4, Raven Press, New York, U.S.

*Primary Examiner* — San-Ming Hui
(74) *Attorney, Agent, or Firm* — Schmesier, Olsen & Watts, LLP

(57) ABSTRACT

The present invention relates to the diuretic effects of nitrate esters of corticoid compounds. A patient in heart failure may be treated by administering a therapeutically effective dosage of a pharmaceutical composition comprising a nitrate ester of corticoid compound as a diuretic having the general formula B—$X_1$—$NO_2$. A method of improving kidney function by administering a therapeutically effective dosage of a pharmaceutical composition having a nitrate ester of corticoid compound of the same formula is also described.

11 Claims, No Drawings

NITRATE ESTERS OF CORTICOID COMPOUNDS USEFUL AS DIURETICS

CROSS REFERENCE TO RELATED APPLICATION

This application claims priority to U.S. Provisional Patent Application to Chao Liu, et al, entitled "Nitrate Esters of Corticoid Compounds Useful as Diuretics" Ser. No. 61/352,254, filed Jun. 7, 2010, the disclosure of which is hereby incorporated entirely herein by reference

BACKGROUND OF THE INVENTION

Technical Field

This invention relates generally to a method of using pharmaceutical compositions having corticoid nitrate derivatives as a diuretic. More specifically, the invention relates to a method of treating a patient with a pharmaceutical composition having corticoid nitrate esters to improve kidney function.

Heart failure (HF) is a major and growing public health problem in the world. Over 5 million individuals in the United States alone have HF and this condition is one of the leading causes of deaths in the western world. As a complex clinical hemodynamic disorder, HF is characterized by progressive pump failure and fluid accumulation. One out of three patients with HF is resistant to diuretic therapy, and developed fluid accumulation. See Ravnan, S. L., Ravnan, M. C. & Deedwania, P. C. Pharmacotherapy in congestive heart failure: diuretic resistance and strategies to overcome resistance in patients with congestive heart failure. *Congest Heart Fail* 8, 80-85 (2002). Atrial natriuretic peptide (ANP) has potent body fluid-eliminating effects in normal physical setting. See Potter, L. R., Abbey-Hosch, S. & Dickey, D. M. Natriuretic peptides, their receptors, and cyclic guanosine monophosphate-dependent signaling functions. *Endocr Rev* 27, 47-72 (2006).

Since ANP was discovered in 1981, people have been trying to use it in the treatment of HF with fluid accumulation. However, all attempts have failed eventually because patients with HF become resistant to both endogenously secreted and exogenously administered ANP. See de Bold, A. J., Borenstein, H. B., Veress, A. T. & Sonnenberg, H. A rapid and potent natriuretic response to intravenous injection of atrial myocardial extract in rats. *Life Sci* 28, 89-94 (1981); Schrier, R. W. & Abraham, W. T. Hormones and hemodynamics in heart failure. N Engl J Med 341, 577-585 (1999). This resistance is due to reduced renal natriuretic peptide receptor A (NPR-A) density in HF. See Bryan, P. M., Xu, X., Dickey, D. M., Chen, Y. & Potter, L. R. Renal hyporesponsiveness to atrial natriuretic peptide in congestive heart failure results from reduced atrial natriuretic peptide receptor concentrations. *Am J Physiol Renal Physiol* 292, F1636-1644 (2007); Schrier, R. W. & Abraham, W. T. Hormones and hemodynamics in heart failure. *N Engl J Med* 341, 577-585 (1999); Michel, J. B., et al. Urinary cyclic guanosine monophosphate as an indicator of experimental congestive heart failure in rats. *Cardiovasc Res* 24, 946-952 (1990); and Yechieli, H., Kahana, L., Haramati, A., Hoffman, A. & Winaver, J. Regulation of renal glomerular and papillary ANP receptors in rats with experimental heart failure. *Am J Physiol* 265, F119-125 (1993).

ANP plays a crucial role in body fluid control. Blood volume expansion acts directly on the heart by stretch of atrial myocytes to increase the release of ANP, which activates renal natriuretic peptide receptor A (NPR-A) and induces potent diuresis. However, since the discovery of ANP, people are frustrated by the fact that its favorable effects are blunted in the diseases with body fluid overload, such as, decompensated heart failure. Moreover, ANP levels in the circulation are proportional to the severity of systemic volume overload and mortality. In the kidney, renal tubular epithelial cells, especially the medullary collecting duct (MCD) cells are the primary site for renal water and sodium excretion, which are also the primary sites for ANP's action.

Therefore, there is a need to develop pharmaceutical compositions which could increase the density of NPR-A in renal tubular epithelial cells, especially the medullary collecting duct (MCD) cells, which potentiates ANP's action in the kidney. There is a further need to develop diuretics for use with diseases which result in severe body fluid and sodium retention. Natriuretic peptide resistance in heart failure is a major problem faced by physicians. There is still a further need for physicians treating heart failure to develop drugs that could upregulate NPR-A in renal tubular epithelial cells.

DISCLOSURE OF THE INVENTION

The present invention relates to the diuretic effects of nitrate esters of corticoid compounds. The nitrate esters of corticoid compounds of the present invention have the general formula:

$$B-X_1-NO_2 \qquad (1)$$

or their esters or salts, where B has the following structure:

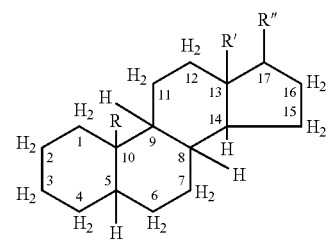

where, in place of the hydrogens H in the CH groups or two hydrogens $H_2$ in the $CH_2$ group shown in the general formula, there may be the following substituents:

at position 1-2: there may be a double bond;
at position 2-3: there may be the following substituent:

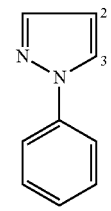

at position 2: there may be Cl, Br;
at position 3: there may be =O, —O—$CH_2$—$CH_2$—Cl, OH;
at position 4-5: there may be a double bond;
at position 5-6: there may be a double bond;
at position 6: there may be Cl, F, $CH_3$, —CHO;
at position 7: there may be Cl;
at position 9: there may be Cl, F;
at position 11: there may be OH, CO, Cl;
at position 16: there may be $CH_3$, OH, =$CH_2$;
at position 17: In addition to R", the other H can be substituted with the following: OH, $CH_3$, OCO(O)$_{ua}$($CH_2$)$_{va}$$CH_3$, or

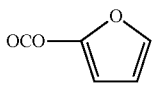

where ua is an integer equal to 0 or 1, va is an integer from 0 to 4;
at positions 16-17: there may be the following groups:

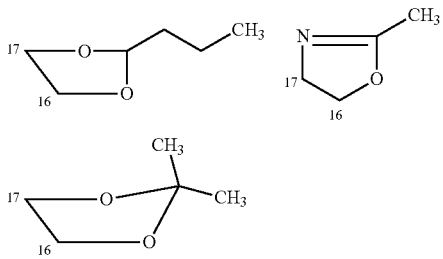

R and R' are equal or different one from the other and may be hydrogen or linear or branched alkyls having from 1 to 4 carbon atoms, preferably R=R'=$CH_3$;
B being a corticosteroid residue;
R" is —(CO-L)$_t$-(X)$_{t1}$—
where t and $t_1$ are integers equal or different one from the other and equal to 0 or 1, provided that they cannot be both equal to 0 when B contains no —OH groups;
the bivalent bridging group L is selected from:

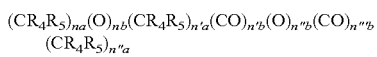

where na, n'a and n"a are equal or different one from the other and are integers from 0 to 6, preferably from 1 to 3; nb, n'b, n"b and n'"b are equal or different one from the other and are integers equal to 0 or 1; $R_4$ and $R_5$ are equal or different one from the other and are chosen from H, linear or branched alkyl having from 1 to 5 carbon atoms, preferably from 1 to 3;
X is equal to $X_0$=O, NH, $NR_{1C}$ where $R_{1C}$ is a linear or branched alkyl having from 1 to 10 C atoms; or equal to $X_2$ where $X_2$ is equal to OH, $CH_3$, Cl, N(—$CH_2$—$CH_3$)$_2$, $SCH_2F$, SH,

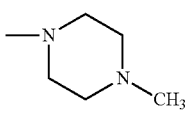

$X_1$ is a bivalent connecting bridge chosen from:
YO, where Y is a linear or whenever possible branched $C_1$-$C_{20}$ alkylene, preferably having from 2 to 5 carbon atoms, or an optionally substituted cycloalkylene having from 5 to 7 carbon atoms;
$Y_1$ selected from:

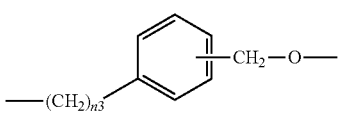

where $n_3$ is an integer from 0 to 3;

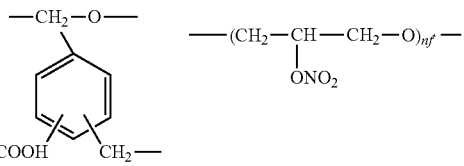

where nf' is an integer from 1 to 6, preferably from 2 to 4;

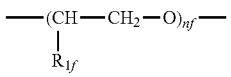

where $R_{1f}$=H, $CH_3$ and nf is an integer from 1 to 6, preferably from 2 to 4.

The compounds which can be mentioned, and which are those preferred, are the ones listed below where B can be obtained according to the known processes of the art. For example, the precursors and related processes described for example in The Merck Index, 12th Ed. of 1996, herein incorporated by reference, can be mentioned as precursors and related processes. The precursors (according to the Merck nomenclature) include the following, where $H_2$, H, R, R', R" have the meaning as defined in the compounds listed below: budesonide, hydrocortisone, alclometasone, algestone, beclomethasone, betamethasone, chloroprednisone, clobetasol, clobetasone, clocortolone, cloprednol, cortisone, corticosterone, deflazacort, desonide, desoximetasone, dexamethasone, diflorasone, diflucortolone, difluprednate, fluazacort, flucloronide, flumethasone, flunisolide, fluocinolone acetonide, fluocinonide, fluocortyn butyl, fluocortolone, fluorometholone, fluperolone acetate, fluprednidene acetate, fluprednisolone, flurandrenolide, formocortal, halcinonide, halobetasol propionate, halometasone, halopredone acetate, hydrocortamate, loteprednol etabonate, medrysone, meprednisone, methylprednisolone, mometasone furoate, parametasone, prednicarbate, prednisolone, prednisolone 25-diethylaminoacetate, prednisolone sodium phosphate, prednisone, prednival, prednylidene, rimexolone, triamcinolone, triamcinolone acetonide, 21-acetoxypregnenolone, cortivazol, amcinonide, fluticasone proprionate, mazipredone, tixocortol, triamcinolone hexacetonide, as described in U.S. Pat. Nos. 7,368,442, 7,205,288, 7,196,075, 7,157,450, 6,610,676, 7,160,871, and 7,056,905, which are incorporated entirely herein by reference.

Accordingly, the present invention relates to a method of treating a patient with heart failure by administering a therapeutically effective dosage of a pharmaceutical composition comprising a nitrate ester of a corticoid compound described by formula (1).

In addition the present invention relates to a method of improving kidney function by administering a therapeutically effective dosage of a pharmaceutical composition comprising a nitrate ester of a corticoid compound described by formula (1). The nitrate esters of corticoid compounds potentiate the natriuretic peptides' action in the kidney.

The foregoing and other features and advantages of the present invention will be apparent from the following more detailed description of the particular embodiments of the invention.

DETAILED DESCRIPTION OF EMBODIMENTS OF THE INVENTION

The present invention relates to a method of using pharmaceutical compositions having nitrate esters of corticoid compounds as diuretics. It has now been found that pharmaceutical compositions having nitrate esters of corticoid compounds have potent diuretic effects in heart failure with body fluid retention. Generally, diuretic effects are described as the ability of the kidney to excrete water and sodium.

The nitrate esters of corticoid compounds of the present invention have the general formula:

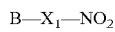    (1)

or their esters or salts, where B has the following structure:

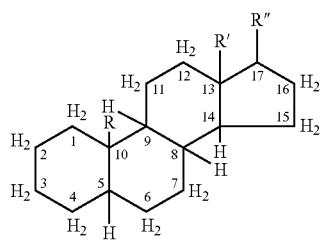

where, in place of the hydrogens H in the CH groups or two hydrogens $H_2$ in the $CH_2$ group shown in the general formula, there may be the following substituents:
at position 1-2: there may be a double bond;
at position 2-3: there may be the following substituent:

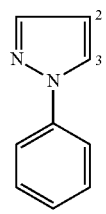

at position 2: there may be Cl, Br;
at position 3: there may be =O, —O—$CH_2$—$CH_2$—Cl, OH;
at position 4-5: there may be a double bond;
at position 5-6: there may be a double bond;
at position 6: there may be Cl, F, $CH_3$, —CHO;
at position 7: there may be Cl;
at position 9: there may be Cl, F;
at position 11: there may be OH, CO, Cl;
  at position 16: there may be $CH_3$, OH, =$CH_2$;
at position 17: In addition to R", the other H can be substituted with the following: OH, $CH_3$, OCO(O)$_{ua}$($CH_2$)$_{va}$$CH_3$, or

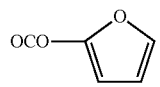

where ua is an integer equal to 0 or 1, va is an integer from 0 to 4;
at positions 16-17: there may be the following groups:

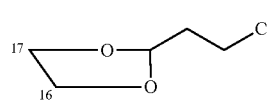 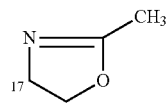

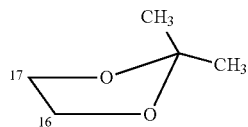

R and R' are equal or different one from the other and may be hydrogen or linear or branched alkyls having from 1 to 4 carbon atoms, preferably R=R'=$CH_3$;

B being a corticosteroid residue;

R" is —(CO-L)$_t$-(X)$_{t1}$ where t and $t_1$ are integers equal or different one from the other and equal to 0 or 1, provided that they cannot be both equal to 0 when B contains no —OH groups; the bivalent bridging group L is selected from:

$(CR_4R_5)_{na}(O)_{nb}(CR_4R_5)_{n'a}(CO)_{n'b}(O)_{n''b}(CO)_{n'''b}$
$(CR_4R_5)_{n''a}$ where na, n'a and n"a are equal or different one from the other and are integers from 0 to 6, preferably from 1 to 3; nb, n' b, n"b and n'''b are equal or different one from the other and are integers equal to 0 or 1; $R_4$ and $R_5$ are equal or different one from the other and are chosen from H, linear or branched alkyl having from 1 to 5 carbon atoms, preferably from 1 to 3;

X is equal to $X_0$=0, NH, $NR_{1C}$ where $R_{1C}$ is a linear or branched alkyl having from 1 to 10 C atoms; or equal to $X_2$ where $X_2$ is equal to OH, $CH_3$, Cl, N(—$CH_2$—$CH_3$)$_2$, $SCH_2F$, SH,

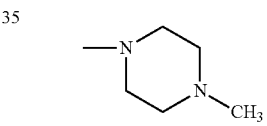

$X_1$ is a bivalent connecting bridge chosen from:

YO, where Y is a linear or whenever possible branched $C_1$-$C_{20}$ alkylene, preferably having from 2 to 5 carbon atoms, or an optionally substituted cycloalkylene having from 5 to 7 carbon atoms;

$Y_1$ selected from:

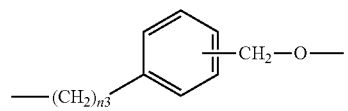

where $n_3$ is an integer from 0 to 3;

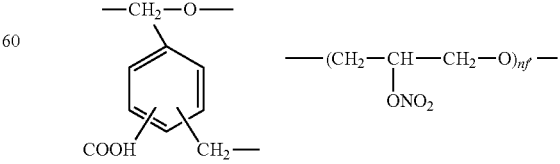

where nf' is an integer from 1 to 6, preferably from 2 to 4;

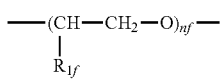

where $R_{1f}$=H, $CH_3$ and nf is an integer from 1 to 6, preferably from 2 to 4.

The compounds which can be mentioned, and which are those preferred, are the ones listed below where B can be obtained according to the known processes of the art. For example, the precursors and related processes described for example in The Merck Index, 12th Ed. of 1996, herein incorporated by reference, can be mentioned as precursors and related processes. The precursors (according to the Merck nomenclature) include the following, where $H_2$, H, R, R', R" have the meaning as defined in the compounds listed below: budesonide, hydrocortisone, alclometasone, algestone, beclomethasone, betamethasone, chloroprednisone, clobetasol, clobetasone, clocortolone, cloprednol, cortisone, corticosterone, deflazacort, desonide, desoximetasone, dexamethasone, diflorasone, diflucortolone, difluprednate, fluazacort, flucloronide, flumethasone, flunisolide, fluocinolone acetonide, fluocinonide, fluocortyn butyl, fluocortolone, fluorometholone, fluperolone acetate, fluprednidene acetate, fluprednisolone, flurandrenolide, formocortal, halcinonide, halobetasol propionate, halometasone, halopredone acetate, hydrocortamate, loteprednol etabonate, medrysone, meprednisone, methylprednisolone, mometasone furoate, parametasone, prednicarbate, prednisolone, prednisolone 25-diethylaminoacetate, prednisolone sodium phosphate, prednisone, prednival, prednylidene, rimexolone, triamcinolone, triamcinolone acetonide, 21-acetoxypregnenolone, cortivazol, amcinonide, fluticasone proprionate, mazipredone, tixocortol, triamcinolone hexacetonide, as described in U.S. Pat. Nos. 7,368,442, 7,205,288, 7,196,075, 7,157,450, 6,610,676, 7,160,871, and 7,056,905, which are incorporated entirely herein by reference.

In addition, U.S. Pat. Nos. 7,605,151, 5,824,669, 5,837,698, 6,197,762, 6,579,863, and 7,056,905, incorporated herein by reference, disclose nitrate esters of corticoid compounds.

The diuretic effect induced by the nitrate esters of corticoid compounds according to the invention is both dose and time dependent. Of note, human response to prednisone, another glucocorticoid, is rather slow. There is usually a 3- or 4-day (sometimes even longer) silent waiting period for the diuretic effects of prednisone therapy to burst out (Liu C, Chen H, Zhou C, Ji Z, Liu G, Gao Y, et al. Potent potentiating diuretic effects of prednisone in congestive heart failure. J Cardiovasc Pharmacol. 2006; 48(4): 173-6.). The lag time of diuretic effects induced by prednisone and the dosage of prednisone (1 mg/kg/day) in humans hampers its use in clinical practice.

We have now found that nitrate esters of corticoid compounds according to the invention can dramatically upregulate the NPR-A expression in renal tubular epithelial cells in much shorter time and with much lower dose in vitro study when compared with their parent compounds. (For example, it takes about half the time and about 1/10 of the dose of NCX-1015 [prednisolone nitrate ester derivatives] to attain the same effect of prednisolone on renal NPR-A in vitro. Nitric oxide (NO)-donating group of nitrate esters of corticoid compounds may synergize with the glucocorticoid drug moiety to produce a more potent diuretic effect. Suitable nitrate esters of corticoid compounds include but are not limited to NCX-1015 (NO-prednisolone): prednisolone 21-[(4'-nitro-oxymethyl)benzoate] having the chemical structure:

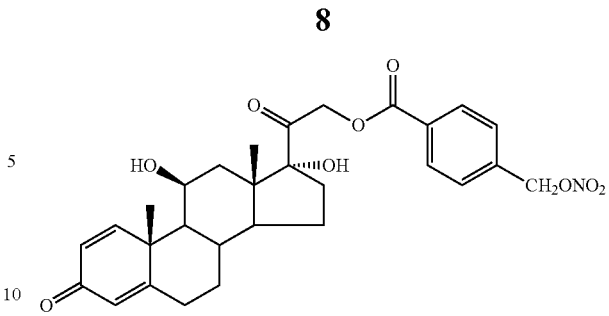

and NCX-1022 (NO-hydrocortisone): hydrocortisone 21-[4'-(nitro-oxymethyl)benzoate having the chemical structure:

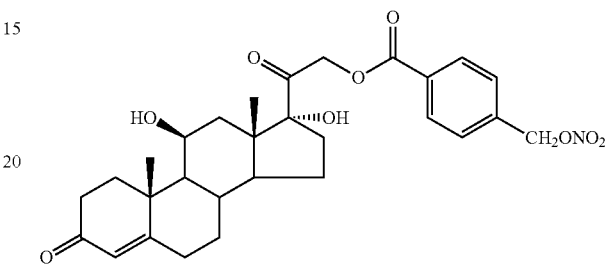

We have found that pharmaceutical compositions having nitrate esters of corticoid compounds are sensitizers of natriuretic peptide, such as ANP and B-type natriuretic peptide (BNP). They can increase the density of NPR-A in renal tubular epithelial cells, especially renal MCD cells, therefore potentiating ANP's action in heart failure. Consistent with the physiological consequences of ANP's action, pharmaceutical compositions having nitrate ester of corticoid compounds administration produces potent diuresis and natriuresis.

Results received point to the possibility that nitrate esters of corticoid compounds according to the invention may produce potent diuretic effects in patients with heart failure. It is believed that the diuretic effects induced by nitrate esters of corticoid compounds are glucocorticoid receptor (GR) mediated and can be abolished by GR antagonist RU 486 (i.e. mifepristone). The corticoid nitrate esters of the present invention induced potent diuretic effects are mediated by upregulation of the natriuretic peptide receptor A (NPR-A) in renal tubular epithelial cells, particularly the MCD cells. It has now been found that pharmaceutical compositions having nitrate esters of corticoid compounds increase the density of NPR-A in renal tubular epithelial cells, especially the MCD cells in vitro and promote their cyclic guanosine monophosphate (cGMP, the second messenger for the natriuretic effects of atrial natriuretic peptide) generation in both a time- and dose-dependent manner.

In vivo, systemic administration with pharmaceutical compositions having nitrate esters of corticoid compounds of the present invention produce potent diuresis in the rats with decompensated heart failure given ad libitum access to food and water, and there was no diuresis-induced increase in water drinking, therefore leading to remarkable systemic volume depletion. Thus, therapy with pharmaceutical compositions having nitrate esters of corticoid compounds according to the method of the present invention represents a promising therapeutic strategy for diseases with fluid retention. These effects are glucocorticoid receptor (GR) mediated and are abolished by GR antagonist RU 486 (i.e. mifepristone).

The therapeutically effective dosages are those that contain an effective dose, or an appropriate fraction thereof, of the active ingredient. The therapeutically effective dosage of the nitrate esters of corticoid compounds useful in the present invention is in an amount in the range of 0.001 to about 1000 mg/kg/day. The treatment time is in the range from about 1 to about 360 days.

The pharmaceutical compositions having nitrate esters of corticoid compounds of the present invention release nitric oxide (NO) in biological fluids both demonstrated in vitro and in vivo. NO-donating group of nitrate esters of corticoid compounds can clearly synergize with the glucocorticoid moiety to produce a potent cardiorenal protective effect. It is believed that this synergy is the result of glucocorticoid receptor (GR) nitration by NO-donating group of nitrate esters of corticoid compounds and/or rapid alterations of the microcirculation within minutes of application of a NO donor.

Pharmaceutical compositions comprising the nitrate esters of corticoid compounds according to the invention increase the density of NPR-A in renal tubular epithelial cells, particularly the MCD cells in vitro and vivo. This potentiates ANP's action in the kidney. Therefore, pharmaceutical compositions comprising the nitrate esters of corticoid compounds according to the invention can be used as diuretics in the diseases with severe body fluid and sodium retention, including but not limited to heart failure, and cirrhotic ascites.

Pharmaceutical compositions comprising the nitrate esters of corticoid compounds according to the invention also inhibit renin-angiotensin-aldosterone system (RAAS) in heart failure. The kidney contains all elements of the RAAS. Both angiotensin II (ANG II) and aldosterone has stimulatory effects on sodium reabsorption in the kidney. ANG II take effects by binding to angiotensin II type I ($AT_1$) receptors. Plasma ANG II and aldosterone levels are significantly elevated in decompensated heart failure, accompanied by an increased renal $AT_1$ receptor density. Renal NPR-A activation induced by glucocorticoids can inhibit the activated RAAS. Glucocorticoids not only decreases ANG II and aldosterone levels in the circulation, but also down-regulates $AT_1$ receptor expression in the kidney.

Pharmaceutical compositions comprising the nitrate esters of corticoid compounds according to the invention also inhibit vasopressin axis in heart failure. The actions of arginine vasopressin (AVP) are mediated by plasma membrane receptors. Three different subtypes of vasopressin receptors have been cloned. Only arginine vasopressin receptor 2 ($V_2$) is located in the kidney. AVP causes antidiuresis by activating $V_2$ receptors on the basolateral surface of the principal cells in the collecting duct. Renal NPR-A activation induced by glucocorticoids can down-regulate $V_2$ receptor expression in the kidney. Moreover, NPR-A activation in hypothalamus induced by glucocorticoids can inhibit AVP release into the circulation.

The pharmaceutical compositions of the present invention may be administered, for example by oral, rectal, parenteral route (including subcutaneous, intradermal, intramuscular, intravenous and intraarticular) or by local (dermal, topical, transdermal, osculatory, inhalatory, topical (including dermal, buccal, sublingual, and intraocular) application.

Generally, the pharmaceutical compositions of the present invention are administered by oral administration or intravenous infusion. Suitable methods of oral administration include, but are not limited to oral solid preparations, such as capsules or tablets, or oral liquid preparations. Tablets may be coated by conventional aqueous or nonaqueous techniques.

The pharmaceutical compositions of the present invention may be administered as the raw chemical, or together with one or more pharmaceutically acceptable carriers. Generally, the pharmaceutical compositions of the present invention are prepared by uniformly and intimately admixing the active ingredient with liquid carriers or finely divided solid carriers or both, and then, if necessary shaping the pharmaceutical composition into the desired presentation.

The following examples further illustrate, not limit, the invention.

Example 1

The Effect of Glucocorticoids on Diuretic Effect and NPR-A Expression in Renal Medulla.

TABLE 1

The effect of Dexamethasone (Dex) on diuretic effect and NPR-A expression in renal medulla

| Compound | Dose (mg/kg) | NPR-A expression (100% of vehicle) | Urinary volume (ml/24 h) | Urinary sodium (mmol/24 h) |
|---|---|---|---|---|
| Dex | 1 | 132.2 ± 9.7* | 16.4 ± 2.4* | 3.50 ± 0.39* |
| Vehicle | — | 100.0 ± 10.7 | 8.9 ± 1.1 | 1.69 ± 0.24 |
| Dex + RU486 | Dex (1 mg/kg), RU486 (100 mg/kg) | 95.5 ± 10.2 | 8.6 ± 1.0 | 1.67 ± 0.27 |

The data is expressed as mean ± standard deviation.
*$P < 0.01$ compared with vehicle.
The receptor expressions in renal medulla were assessed by western blotting analysis and expressed as a relative value compared with the average density measured in the vehicle treated rats.

To determine the effect of glucocorticoids on diuretic effect and NPR-A expression in renal medulla, 15 intact Wistar rats were randomized to receive Dexamethasone (Dex), vehicle and glucocorticoid receptor (GR) antagonist RU 486. As shown in Table 1 above, after 24-hour treatment, Dex dramatically increased urinary volume and urinary sodium compared with vehicle treated rats, which was associated with a dramatic NPR-A overexpression. But the diuretic effect and NPR-A expression in renal medulla induced by Dex was completely abolished by RU486, suggesting that the diuretic effect and NPR-A overexpression induced by glucocorticoids was mediated by GR.

Example 2

Study of NPR-A Expression in Inner Medullary Collecting Duct (IMCD) Cells.

TABLE 2

Study of the effect of NCX-1015 versus prednisolone on NPR-A expression in IMCD cells

| Compound | concentration (mol/L) | NPR-A expression (24 hours) | NPR-A expression (48 hours) |
|---|---|---|---|
| NCX-1015 | $10^{-7}$ | ++ | +++ |
| prednisolone | $10^{-6}$ | + | ++ |
| Vehicle | — | + | + |

Density of membrane NPR-A in IMCD cells were visualized by immunofluorescence expressed with the number of "+" (+ = low, ++ = moderate, +++ = high).

IMCD cells from Wistar rats were isolated and cultured using the method previously described by Ye Q et al.: Endothelin inhibits NPR-A and stimulates eNOS gene expression in rat IMCD cells. Hypertension 41, 675-681 (2003). IMCD cells were cultured with Dulbecco's modified Eagle medium plus fetal calf serum that was glucocorticoid free for 3-4 days until the cells attained confluence. The IMCD cells were then treated with NCX-1015, prednisolone, or vehicle for 48 hours. The Density of membrane NPR-A in IMCD cells were visualized by immunofluorescence. As shown in Table 2 above, NCX-1015 dramatically increased NPR-A density in IMCD cells using less time and dose compared with its parent compound prednisolone.

TABLE 3

The effect of NCX-1022 on NPR-A expression in IMCD cells

| Compound | concentration (mol/L) | NPR-A expression (24 hours) | NPR-A expression (48 hours) |
|---|---|---|---|
| NCX-1022 | $10^{-7}$ | ++ | +++ |
| hydrocortisone | $10^{-6}$ | + | ++ |
| Vehicle | — | + | + |

Density of membrane NPR-A in IMCD cells were visualized by immunofluorescence expressed with the number of "+" (+ = low, ++ = moderate, +++ = high).

Similarly, as shown in Table 3 above, NCX-1022 dramatically increased NPR-A density in IMCD cells using less time and dose compared with its parent compound hydrocortisone.

Example 3

Study of Diuretic Effects in Decompensated Heart Failure

TABLE 4

Study of diuretic effect of NCX-1015 versus prednisolone in rats with decompensated heart failure

| compound | Dose (mg/kg) | Urinary volume (ml/12 h) | Urinary sodium (mmol/12 h) |
|---|---|---|---|
| NCX-1015 | 1 | 8.8 ± 1.5*# | 1.43 ± 0.15*# |
| prednisolone | 1 | 6.1 ± 0.7* | 1.08 ± 0.1* |
| Vehicle | — | 3.3 ± 0.5 | 0.72 ± 0.07 |

The data are expressed as mean ± standard deviation.
*$P < 0.05$ compared with vehicle.
$P < 0.05$ compared with prednisolone.

To determine the effects of corticosteroids on systemic volume in HF, 15 Wistar rats with HF were randomized to receive NCX-1015 (n=5), or prednisolone (n=5), or vehicle (n=5). HF model was accomplished by left anterior descending artery ligation, and then the survived rats were raised for 12 weeks to have decompensated HF (i.e. HF with fluid accumulation). Parameters on urinary volume and urinary sodium in 12 hours were collected. As shown in Table 4 above, both NCX-1015 and prednisolone dramatically increased renal water and sodium excretion as compared with vehicle. Of note, NCX-1015 treated rats excreted much more water and sodium than prednisolone treated rats. Western blotting analysis showed that heart failure rats treated with prednisolone or NCX-1015 had higher NPR-A expression in the renal medulla (26.5% higher in prednisolone group, P=0.008; and 42.8% higher in NCX-1015 group, P=0.008; respectively) than did vehicle-treated rats. However, NCX-1015 treated rats had higher NPR-A expression in renal medulla than did prednisolone treated rats (P=0.032).

Example 4

Study of Renin-Angiotensin-Aldosterone System (RAAS) in Decompensated Heart Failure

TABLE 5

Study of NCX-1015 on RAAS in rats with decompensated heart failure

| Compound | Dose (mg/kg) | $AT_1$ receptor density in the kidney (% of vehicle) | Plasma angiotensin II (pg/ml) | Plasma aldosterone (ng/ml) |
|---|---|---|---|---|
| NCX-1015 | 1 | 43.14 ± 7.07*# | 412.20 ± 64.99*& | 0.99 ± 0.09*# |
| Prednisolone | 1 | 67.06 ± 12.96* | 665.86 ± 113.90$ | 1.39 ± 0.26* |
| Vehicle | — | 100.00 ± 9.49 | 878.5 ± 117.91 | 2.16 ± 0.41 |

The data are expressed as mean ± standard deviation.
*$P < 0.01$ compared with vehicle.
$$P < 0.05$ compared with vehicle.
&$P < 0.01$ compared with prednisolone.
$P < 0.05$ compared with prednisolone.
The receptor densities were assessed by western blotting analysis and expressed as a relative value compared with the average density measured in the vehicle treated rats.

To determine the effects of corticosteroids on RAAS in HF, 15 Wistar rats with HF were randomized to receive NCX-1015 (n=5), or prednisolone (n=5), or vehicle (n=5). After 24-hour treatment, as shown in Table 5 above, both NCX-1015 and prednisolone dramatically decreased plasma angiotensin II and aldosterone levels, and $AT_1$ receptor density in the kidney as compared with vehicle. Of note, NCX-1015 is superior over prednisolone in inhibiting RAAS in rats with heart failure.

Example 5

Study of Vasopressin Axis in Decompensated Heart Failure

TABLE 6

Study of NCX-1015 on vasopressin axis in rats with decompensated heart failure

| compound | Dose (mg/kg) | $V_2$ receptor density in the kidney (% of vehicle) | Plasma vasopressin (pg/ml) |
|---|---|---|---|
| NCX-1015 | 1 | 54.06 ± 16.15*# | 32.14 ± 5.47*# |
| prednisolone | 1 | 79.80 ± 9.44$ | 45.72 ± 8.35$ |
| Vehicle | — | 100.00 ± 12.82 | 68.26 ± 14.09 |

The data are expressed as mean ± standard deviation.

*P < 0.01 compared with vehicle.

$P < 0.05 compared with vehicle.

P < 0.05 compared with prednisolone.

The receptor densities were assessed by western blotting analysis and expressed as a relative value compared with the average density measured in the vehicle treated rats.

To determine the effects of corticosteroids on vasopressin axis in HF, 15 Wistar rats with HF were randomized to receive NCX-1015 (n=5), or prednisolone (n=5), or vehicle (n=5). After 24-hour treatment, as shown in Table 6 above, both NCX-1015 and prednisolone dramatically decreased plasma vasopressin levels, and $V_2$ receptor density in the kidney as compared with vehicle. NCX-1015 was superior over prednisolone in inhibiting vasopressin axis in rats with heart failure.

The embodiments and examples set forth herein were presented in order to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A method of treating a patient with heart failure by administering a therapeutically effective amount of a pharmaceutical composition comprising a nitrate ester of a corticoid compound wherein the compound is prednisolone 21-[(4'-nitro-oxymethyl)benzoate] having the chemical structure:

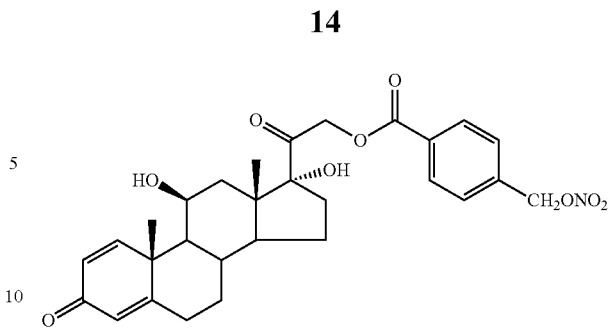

and wherein renal natriuretic peptide receptor A expression in the patient kidney is increased with the therapeutically effective amount of the pharmaceutical composition.

2. A method of treating a patient with heart failure by administering a therapeutically effective amount of a pharmaceutical composition comprising a nitrate ester of a corticoid compound wherein the compound is prednisolone 21-[(4'-nitro-oxymethyl)benzoate] having the chemical structure:

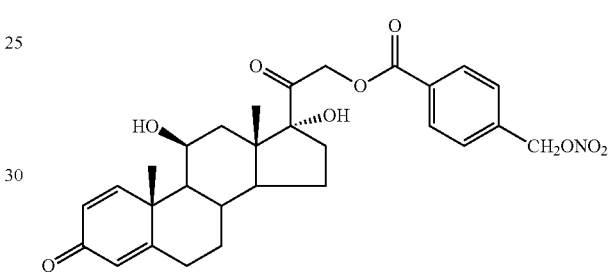

and wherein vasopressin axis is inhibited.

3. The method of claim 2, wherein the therapeutically effective amount of the nitrate ester of the corticoid compound is in an amount in the range of from about 0.001 to about 1000 mg/kg/day.

4. The method of claim 2, wherein treatment time is in the range of from about 1 to about 360 days.

5. A method of treating a patient with heart failure by administering a therapeutically effective amount of a pharmaceutical composition comprising a nitrate ester of a corticoid compound wherein the compound is hydrocortisone 21-[4'-(nitro-oxymethyl)benzoate having the chemical structure:

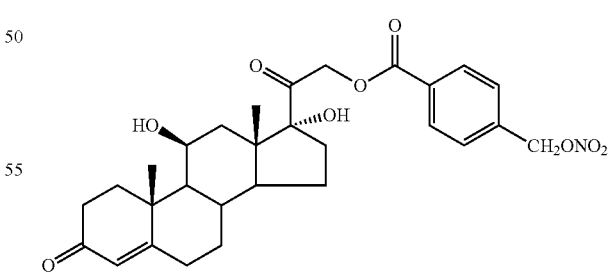

and wherein renal natriuretic peptide receptor A expression in the patient kidney is increased with the therapeutically effective amount of the pharmaceutical composition.

6. The method of claim 5, wherein the therapeutically effective amount of the nitrate ester of the corticoid compound is in an amount in the range of from about 0.001 to about 1000 mg/kg/day.

7. The method of claim 5, wherein treatment time is in the range of from about 1 to about 360 days.

8. The method of claim 1, wherein the therapeutically effective amount of the nitrate ester of the corticoid compound is in an amount in the range of from about 0.001 to about 1000 mg/kg/day.

9. The method of claim 1, wherein treatment time is in the range of from about 1 to about 360 days.

10. The method of claim 1, wherein the therapeutically effective amount of the pharmaceutical composition is a diuretic.

11. The method of claim 1, wherein renin-angiotensin-aldosterone system is inhibited.

* * * * *